US009775629B1

(12) United States Patent
    Henderson (10) Patent No.: US 9,775,629 B1
(45) Date of Patent: Oct. 3, 2017

(54) APPARATUS FOR OSTEOTOMY AND GRAFT PREPARATION

(71) Applicant: Eric Ross Henderson, Boston, MA (US)

(72) Inventor: Eric Ross Henderson, Boston, MA (US)

(73) Assignee: University of South Florida, Tampa, FL (US)

( * ) Notice: Subject to any disclaimer, the term of this patent is extended or adjusted under 35 U.S.C. 154(b) by 419 days.

(21) Appl. No.: 14/565,786

(22) Filed: Dec. 10, 2014

Related U.S. Application Data

(60) Division of application No. 13/359,862, filed on Jan. 27, 2012, now Pat. No. 8,920,426, which is a continuation of application No. PCT/US2010/044247, filed on Aug. 3, 2010.

(60) Provisional application No. 61/231,112, filed on Aug. 4, 2009.

(51) Int. Cl.
    *A61F 2/46* (2006.01)
    *A61B 17/16* (2006.01)

(52) U.S. Cl.
    CPC ........ *A61B 17/1662* (2013.01); *A61F 2/4644* (2013.01); *A61F 2002/4645* (2013.01)

(58) Field of Classification Search
    CPC ........... A61F 2/4644; A61F 2002/4645; B23D 51/02; B23D 51/04
    See application file for complete search history.

(56) References Cited

U.S. PATENT DOCUMENTS

| | | | | |
|---|---|---|---|---|
| 3,988,814 | A | * | 11/1976 | Hoffman ................... B23C 1/06 144/46 |
| 4,565,192 | A | * | 1/1986 | Shapiro ................ A61B 17/158 606/82 |
| 5,190,547 | A | | 3/1993 | Barber, Jr. et al. |
| 5,569,254 | A | | 10/1996 | Carlson et al. |
| 5,569,256 | A | | 10/1996 | Vaughn et al. |
| 6,007,541 | A | | 12/1999 | Scott |
| 6,025,538 | A | | 2/2000 | Yaccarino, III |
| 6,508,841 | B2 | | 1/2003 | Martin et al. |

(Continued)

FOREIGN PATENT DOCUMENTS

WO        2011017321 A3      2/2011

OTHER PUBLICATIONS

International Search Report for International application No. PCT/US2010/044247 filed on Aug. 30, 2010, dated Mar. 24, 2011, applicant University of South Florida et al.

(Continued)

*Primary Examiner* — Nicholas Woodall
(74) *Attorney, Agent, or Firm* — Nilay J. Choksi; Smith & Hopen, P.A.

(57) ABSTRACT

Surgical tools that increase surgical accuracy for orthopedic procedures involving long bone osteotomy with or without supplementation with allograft or autograft. Two clamps on the operative side are rigidly interconnected to one another with an adjustable rod that is locked into place, preserving length and rotation of the bone. A graft preparation device is used on the operative table. It enables alignment of the graft to preserve the desired mechanical and anatomic axes and to provide rigid fixation of the graft for cutting. Adjustable jigs ensure exact cuts.

21 Claims, 8 Drawing Sheets

(56) References Cited

U.S. PATENT DOCUMENTS

| | | | |
|---|---|---|---|
| 6,557,226 B1* | 5/2003 | Landry | A61F 2/28 29/27 A |
| 6,565,570 B2 | 5/2003 | Sterett et al. | |
| 6,800,093 B2 | 10/2004 | Nicholson et al. | |
| 6,884,246 B1 | 4/2005 | Sonnabend et al. | |
| D601,250 S * | 9/2009 | Haunschild | D24/133 |
| 8,535,315 B2* | 9/2013 | Wong | A61B 17/1635 606/79 |
| 2003/0018338 A1 | 1/2003 | Axelson, Jr. et al. | |
| 2005/0125062 A1* | 6/2005 | Biedermann | A61F 2/442 623/17.11 |
| 2006/0015109 A1 | 1/2006 | Haines | |
| 2008/0177297 A1 | 7/2008 | Steiner et al. | |
| 2008/0255623 A1* | 10/2008 | Steiner | A61F 2/4644 606/86 R |
| 2013/0096680 A1* | 4/2013 | Ribeiro | A61F 2/3872 623/14.12 |

OTHER PUBLICATIONS

International Preliminary Report on Patentability for International application No. PCT/US2010/044247 filed on Aug. 30, 2010, dated Feb. 16, 2012, applicant University of South Florida et al.

\* cited by examiner

APPARATUS FOR OSTEOTOMY AND GRAFT PREPARATION

CROSS-REFERENCE TO RELATED APPLICATIONS

This application is a divisional of and claims priority to U.S. Nonprovisional application Ser. No. 13/359,862, entitled "Apparatus for Osteotomy and Graft Preparation", filed Jan. 27, 2012, which is a continuation of and claims priority to PCT Application No. PCT/US2010/044247, entitled "Apparatus for Osteotomy and Graft Preparation", filed Aug. 3, 2010, which claims priority to U.S. Provisional Application No. 61/231,112, entitled "Apparatus for Osteotomy and Graft Preparation", filed Aug. 4, 2009, all of which are incorporated herein by reference in their entireties.

BACKGROUND OF THE INVENTION

1. Field of the Invention

This invention relates, generally, to tools used in orthopedic surgery. More particularly, it relates to tools that enable resection of patient bone in the setting of trauma or bone tumors and the accurate preparation of allograft to fill deficient patient bone after resections.

2. Brief Description of the Related Art

Allograft (bone harvested from human cadavers) is used commonly in orthopedic tumor surgery and is also used to replace bony deficits in orthopedic trauma surgery. Following resection of small and large pieces of bone for the cure of bone tumors, allograft replacements for the resected bone are fashioned from bulk specimens of treated cadaver bone. In procuring these replacement parts, healing is facilitated by an anatomic (accurate) fit of the allograft replacement. Electric reciprocating saws, which are difficult to guide, are used to cut allograft replacement parts. When used for total knee replacement, these saws are used in conjunction with metal jigs that guide the saw blade and ensure accurate cuts. Such guides, however, are not currently available for use for shaping allograft to replace bone deficits.

Accordingly, what is needed in the art are specially designed clamps and jigs for use in the operating room to aid both in the accurate resection of patient bone and the preparation of cadaver bone. However, in view of the prior art considered as a whole at the time the present invention was made, it was not obvious to those of ordinary skill in the art how the limitations of the art could be overcome.

However, in view of the art considered as a whole at the time the present invention was made, it was not obvious to those of ordinary skill in the field of this invention how the shortcomings of the prior art could be overcome.

BRIEF SUMMARY OF THE INVENTION

The long-standing but heretofore unfulfilled need for improved tools for use in orthopedic surgery is now met by a new, useful, and non-obvious invention.

The inventive structure includes a plurality of tools for use in the operating room that aid both in the accurate resection of patient bone and the preparation of cadaver bone. The devices include bone clamps with interchangeable jigs that are applied to the patient's bone in surgery and a device used on the "back table" in the operating room that includes bone clamps and cutting jigs to prepare a reciprocal piece of allograft that will interdigitate with the patient's bone.

The clamps are modifications of the conventional Lane bone clamp or self-centering bone forceps and include a handle and forceps for grasping a bone.

The bone resection device includes a pair of bone clamps each having a handle end and a clamping end. A pair of receiving slots is disposed on the clamping ends of each clamp. Both pairs of receiving slots are adapted to receive a cutting jig. Curved struts extend from the top surface of the clamping end of each clamp. The distal ends of the curved struts include receiving holes. A securing rod is disposed between the curved struts within the receiving holes. The securing rod rigidly interconnects the clamps.

The allograft preparation device includes a tabletop having a plurality of parallel, longitudinally extending grooves formed therein. A first pair of blocks is slideably disposed in a preselected groove of the plurality of grooves. The first pair of blocks includes circular discs pointing to a center of the tabletop. The circular discs include stationary sharpened points at a center of the discs to align an anatomic axis of an allograft piece by pressing the allograft piece into the sharpened points.

A second pair of movable blocks is secured in a preselected groove of the plurality of grooves. The second pair of blocks support adjustable arms that hold bone clamps (similar to the ones described above) that secure the allograft piece against movement. Once the allograft piece is secured against movement by the bone clamps, the first pair of blocks is retracted.

A third pair of blocks is slideably disposed in a preselected groove of the plurality of grooves and holds cutting jigs that are mounted to a cylinder that, prior to being secured against movement by a threaded handle, is rotated to adjust a preselected angle of cut as needed.

The novel devices significantly improves results with the use of allograft as tight allograft-to-bone contact is required to encourage adequate healing of patient bone to allograft.

The primary object of this invention is to advance the art of orthopedic surgery by providing tools that aid a surgeon in performing accurate resection of patient bone and the preparation of cadaver bone.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

The novel system increases surgical accuracy for orthopedic procedures involving long bone osteotomy with or without supplementation with allograft or autograft. Difficulties with long bone osteotomy with or without graft placement include obtaining the desired final length, preventing malrotation of the osteotomized ends, ensuring exact fit of the united bone ends, and maintaining all of these elements with stability when final fixation is applied. Additional difficulties arise when using an interposition graft as the graft must be prepared so as not to disrupt the long bone's anatomic or mechanical axes. This invention addresses these aspects of long bone osteotomy and graft preparation.

The novel system has two components. On the operative side, a bone resection device includes two clamps (these may be modeled on a Lane bone clamp or a self-centering bone forceps) that are rigidly interconnected to one another with an articulated rectangular rod that is locked into place, preserving length and rotation of the bone. The second component is a graft preparation device used on the operative table. This device enables alignment of the graft to preserve the desired mechanical and anatomic axes. It also secures the graft against movement to facilitate cutting of the graft. Adjustable jigs ensure exact cuts.

Figure 1A:
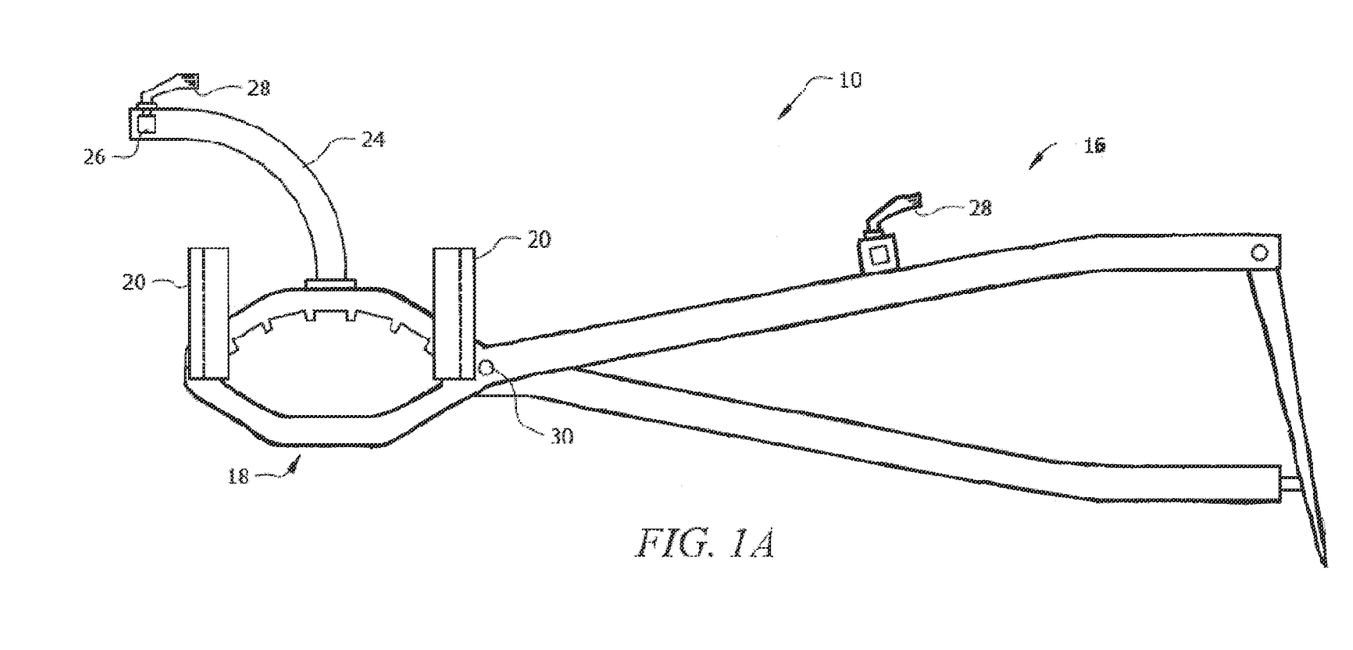
FIG. 1A is a side elevational view of a novel clamp having straight arms.
Figure 1B:
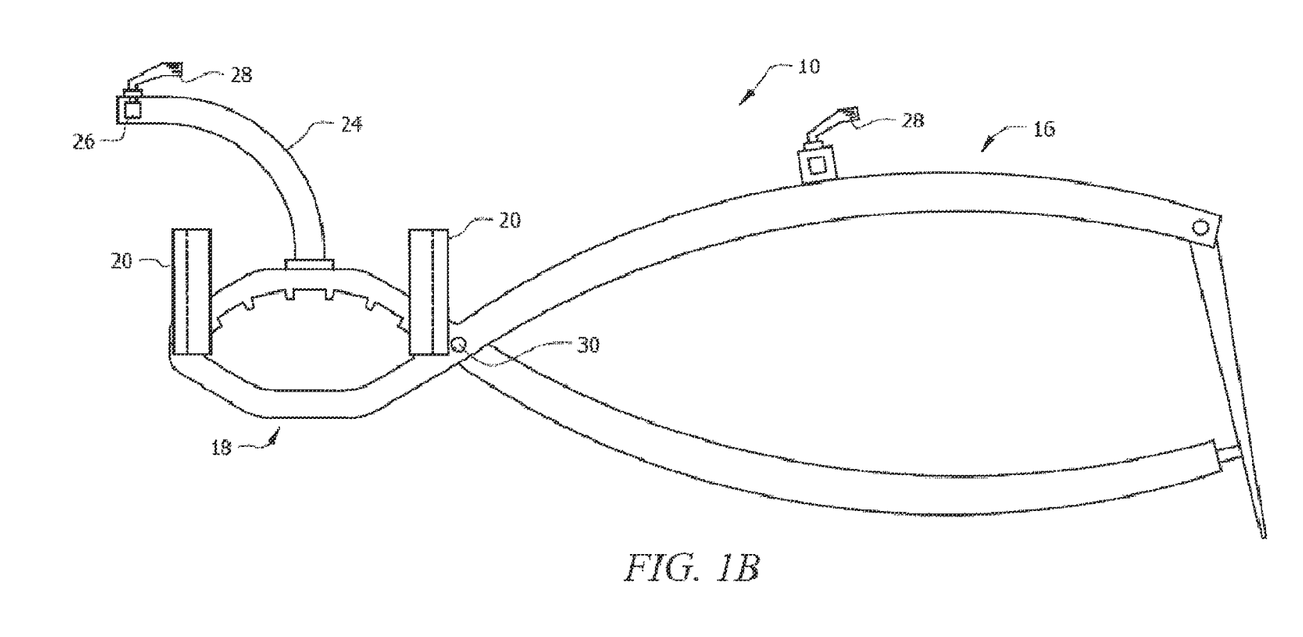
FIG. 1B is a side elevational view of a novel clamp having curved arms.

FIGS. 1A and 1B are diagrammatic representation of clamp 10 having utility in connection with a bone resection device. The clamps include handle end 16 and clamping end 18 that are mechanically engaged via hinge 30. Mechanically, clamp 10 functions like a standard clamp, i.e., as handle end 16 is engaged, clamping end 10 opens and closes. The inner portion of clamping end 18 is notched to accommodate the placement of plates which are used commonly in orthopaedic surgery for fixation. These notches allow the plate(s) to be placed with the clamps in place so that rotational alignment of the cut bone ends is maintained until the plate is secured to the bone and the allograft with bone screws.

Curved strut 24 extends from the top surface of clamping end 18. The distal end of curved strut 24 includes receiving hole 26 and wing nut 28 which are adapted to receive and secure a securing rod as discussed hereafter. Curved strut 24 extends outward and away from handle end 16 to keep the securing rod out of the operative field of a surgeon.

Handle end 18 may be curved (arcuate) or straight to facilitate insertion into deep incisions.

Figure 2:
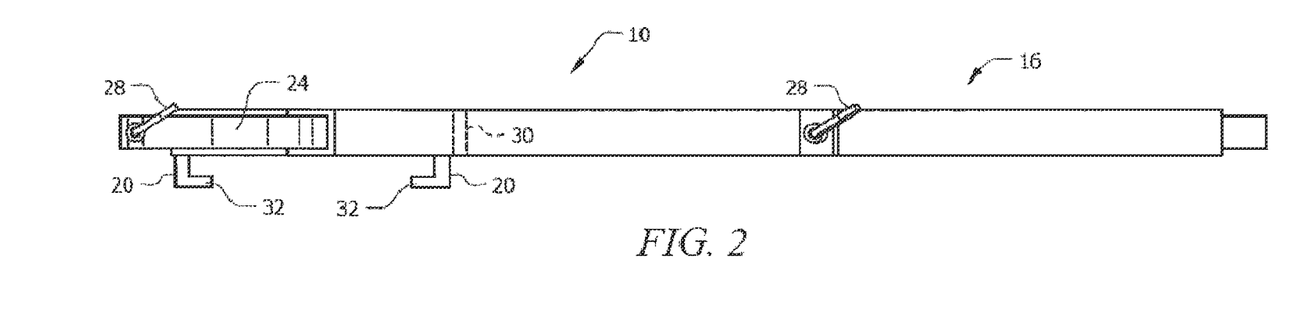
FIG. 2 is a top plan view of the clamps depicted in FIGS. 1A and 1B, said clamps having a common appearance when depicted in plan.

As depicted in FIGS. 1A-2, receiving slots 20 are disposed on clamping end 18 and include two transverse slots. The transverse slots include lip 32 for receiving a cutting jig.

Figure 3:
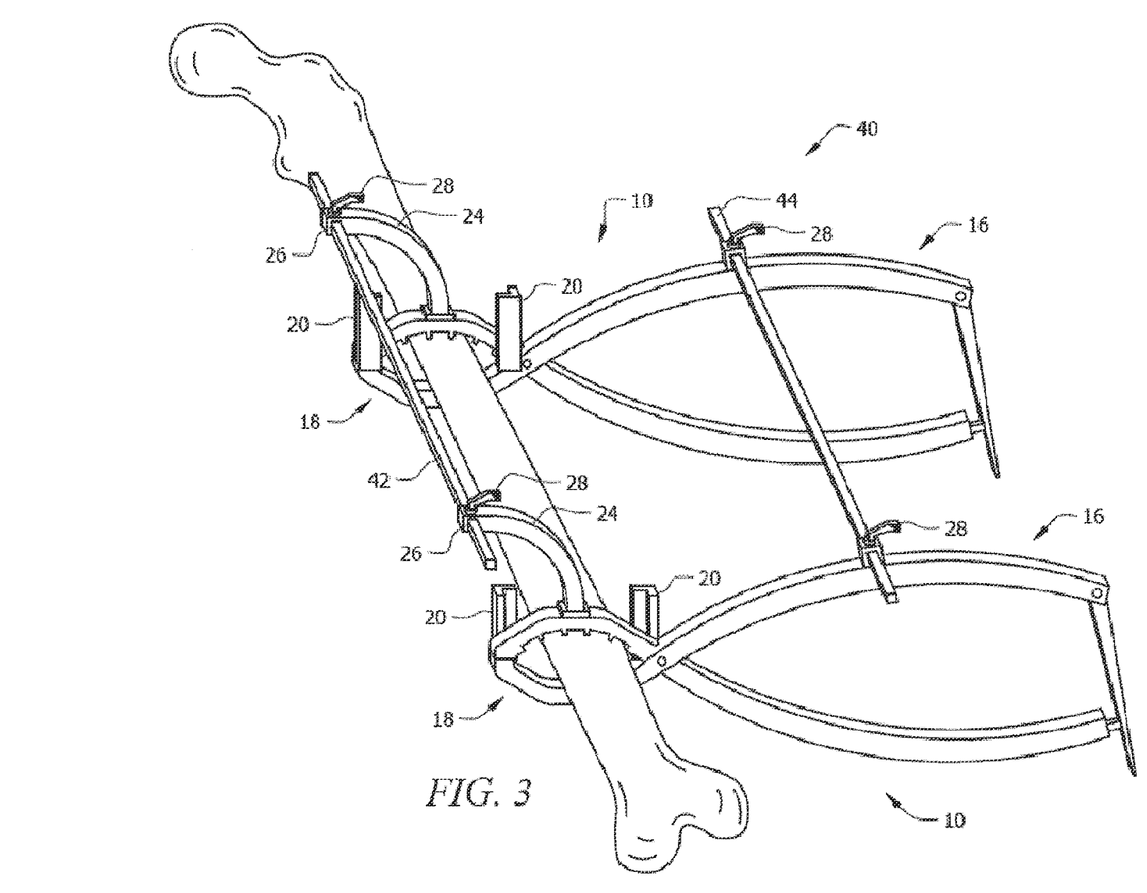
FIG. 3 is a perspective view of a bone resection device.

As depicted in FIG. 3, bone resection device 40 enables a surgeon to preserve the length and rotation of a bone resection. Bone resection device 40 includes a pair of clamps 10 each having handle end 16, clamping end 18, curved strut 24 (with receiving hole 26 and wing nut 28), and receiving slots 20, as previously discussed. A first clamp is placed just proximal to the resection and a second clamp is placed just distal to the resection. Both clamps are locked in a closed, clamping position using a paw and ratchet locking mechanism or a strap to force the handle together. Any known means may be used to secure the clamps.

Still referring to FIG. 3, securing rod 42 is disposed between the curved struts within receiving holes 26 and secured in place via wing nut 28. Accordingly, securing rod 42 rigidly interconnects the clamps. An additional securing rod may be necessary to counteract compression forces from the soft tissues on the bone ends. If necessary, securing rod 44 is disposed between handles 18 of clamps 10. An additional wing nut 28 may be incorporated to secure securing rod 44. As depicted, the securing rods are rectangular metal rods. A rectangular rod prevents rotation between the clamps; however, the rod may be any shape and length necessary to rigidly interconnect the clamps. The securing rods may also include a ruler to record length and assure accurate repositioning. Moreover, the securing rod may include a universal joint that is lockable to a desired angle.

Figure 4A:
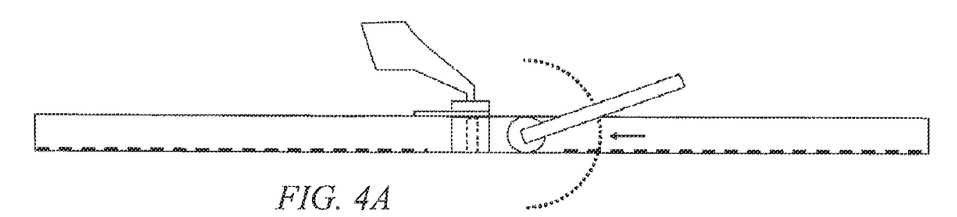
FIG. 4A is a top plan view of an articulated-rectangular interconnecting rod.
Figures 4B, 4C:
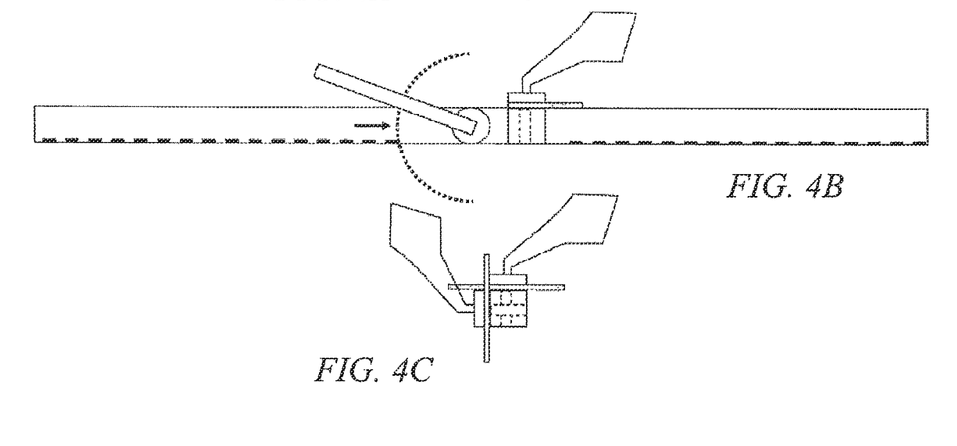
FIG. 4B is a side elevational view of the structure depicted in FIG. 4A.
FIG. 4C depicts two articulated-rectangular interconnecting rods when in perpendicular relation to one another.

FIG. 4A depicts in top plan view the rectangular interconnecting rod that interconnects the two clamps to one another and preserves a fixed length and rotation. FIG. 4B is a side elevational view thereof. A ruler having metric, centimeter and millimeter demarcations is included for taking measurements for the portion of bone to be cut on the 'back table' and for restoring a desired length if the rod must be removed for any reason. In an embodiment, the rod has two rotating joints 60 and 62 located mid-length forming a locking universal joint. Joints 60 and 62 allow rotation of one rod arm with respect to the other in one plane of motion. The joints are placed in perpendicular orientation to one another to allow three-dimensional motion as indicated in FIG. 7C, thus acting as a universal joint. Each joint has a protractor showing one-hundred and eighty degrees of motion. Angle readings from these protractors direct the surgeon to the correct settings of the 'back table' cutting device (discussed hereafter) in order to create an identical allograft replacement. The joints have lockable pivots as indicated by the transverse lines that enable the rod to be fixed rigidly in the orientation of the bone clamps once the clamps have been applied to the bone to be resected.

Figure 5A:
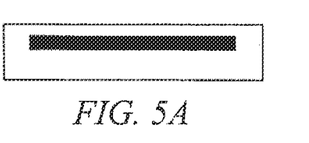
FIG. 5A is a top plan view of a first novel jig.
Figure 5B:
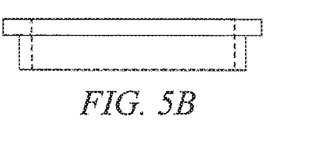
FIG. 5B is a side elevational view of the jig depicted in FIG. 5A.
Figure 5C:
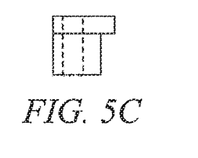
FIG. 5C is an end view of the jig depicted in FIGS. 5A and 5B.
Figure 5D:
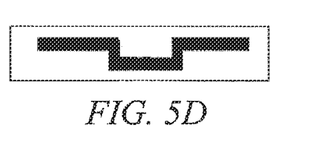
FIG. 5D is a top plan view of a second novel jig.
Figure 5E:
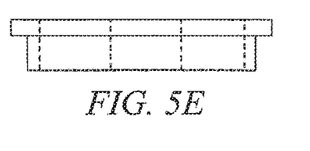
FIG. 5E is a side elevational view of the jig depicted in FIG. 5D.
Figure 5F:
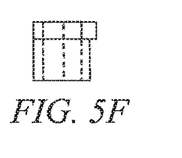
FIG. 5F is an end view of the jig depicted in FIGS. 5D and 5E.
Figure 5G:
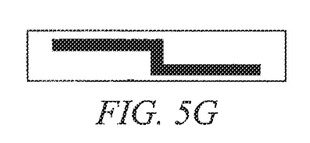
FIG. 5G is a top plan view of a third novel jig.
Figure 5H:
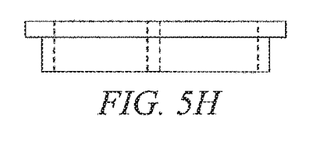
FIG. 5H is a side elevational view of the jig depicted in FIG. 5G.
Figure 5I:
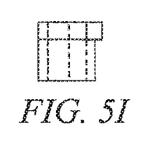
FIG. 5I is an end view of the jig depicted in FIGS. 5G and 5H.

Cutting jigs are disposed within receiving slots 20. Receiving slots 20 are formed to accommodate the smaller dimensions of the cutting jig in FIGS. 5B, 5E, 5H and in FIGS. 5C, 5F, 5I, thereby allowing the larger dimensions in these figures to abut the top of receiving slots 20 to provide a secure fit and prevent fall-through. The cutting jigs are therefore oriented so that the slot that permits passage of a saw blade is perpendicular to the bone. Once the cutting jigs are inserted into receiving slots 20, a typical reciprocating bone saw with an appropriate saw blade can be used to perform the bone cuts.

FIGS. 5A-I depict the types of cutting jigs that accompany the bone clamps shown in FIGS. 1A-3. These cutting jigs enable a surgeon to make transverse cuts, step cuts, notch cuts, or any other type of cut in the bone to be resected.

All of the aforementioned components are preferably made of surgical grade stainless steel; however, other materials may be used.

Figure 6:
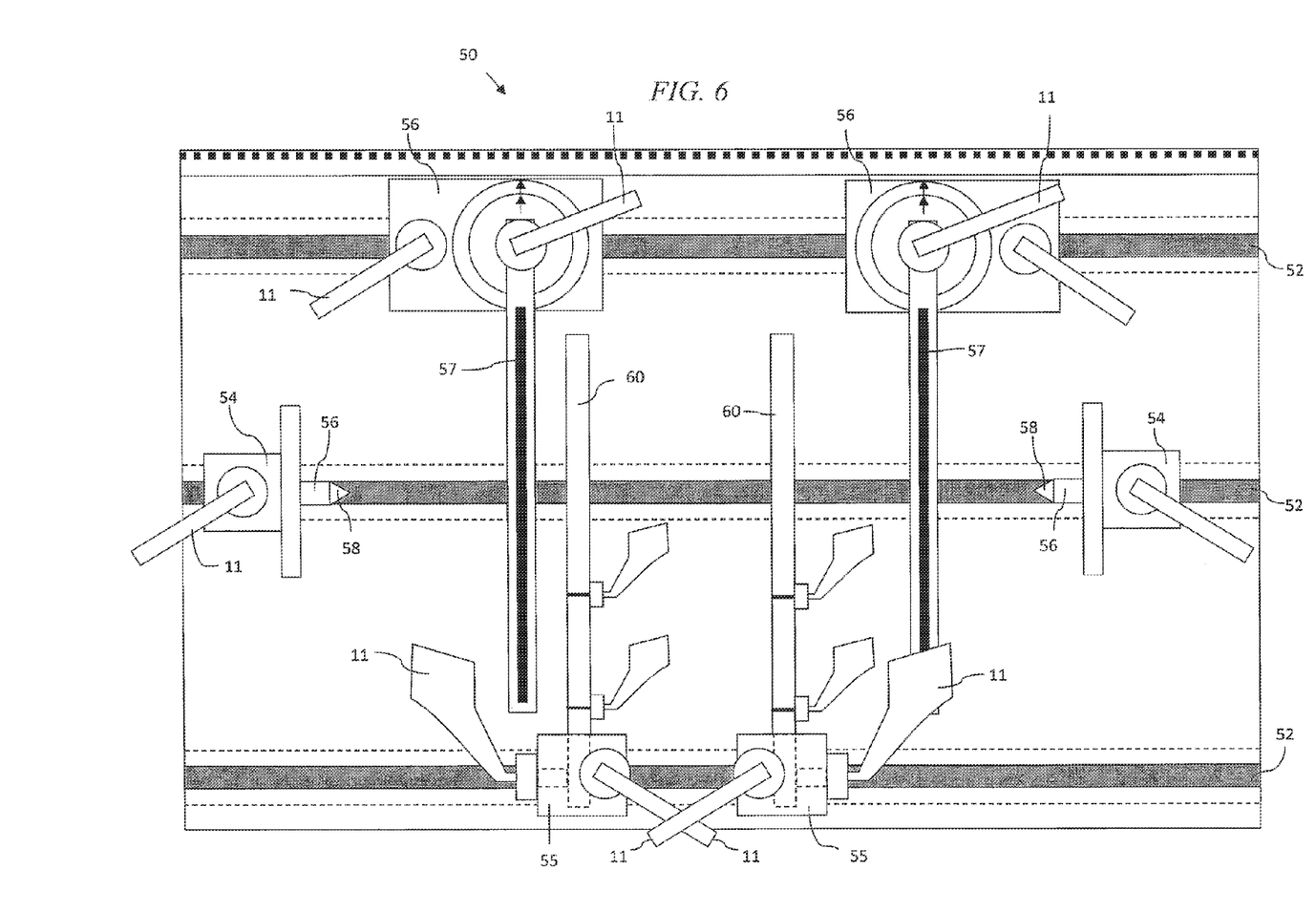
FIG. 6 is a top plan view of a back table allograft cutting device.

FIG. 6 depicts a back table allograft cutting device in plan view. This device is used to cut the allograft to specification for the replacement of the resection. Table top 50 of the cutting device is preferably made of machined stainless steel.

Tabletop 50 has three longitudinally extending grooves formed therein, collectively denoted as 52. Each groove has an inverted "T" configuration. These grooves receive the sliding/locking inverted T-shaped devices that lock the cutting jigs and allograft stabilizing devices to tabletop 50. A ruler is engraved in the tabletop in parallel relation to the grooves.

First pair of stainless steel blocks 54 is slideably mounted in the center groove and have circular discs 56 pointing to the center of the tabletop and sharpened points 58 in the center of the discs. This device aligns the anatomic axis of the allograft piece to be cut by pressing the allograft into the stationary sharpened points 58, enabling the operator to anchor the center of the allograft with a pair of bone clamps 60. Blocks 54 may be retracted to opposite ends of the device after bone clamps 60 are placed into their respective operative configurations. This could be necessary depending on how close to the ends the cuts must be made.

Second pair of blocks 55 is slideably mounted in the lower groove as depicted. Blocks 55 support adjustable arms that hold bone clamps 60 that anchor the allograft to be cut.

Figures 8A, 8B:
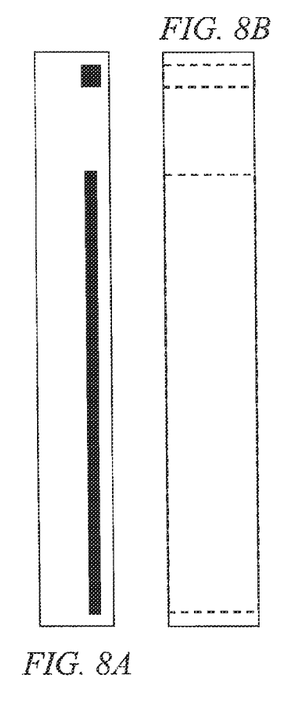
FIG. 8A is a top plan view of a first novel back table allograft cutting jig.
FIG. 8B is a side elevational view of the cutting jig depicted in FIG. 8A.
Figure 8C:
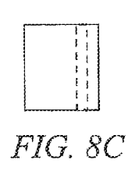
FIG. 8C is an end view of the cutting jig depicted in FIGS. 8A and 8B.
Figure 8D:
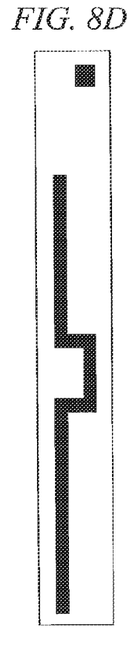
FIG. 8D is a top plan view of a second novel back table allograft cutting jig.
Figures 8E, 8F:
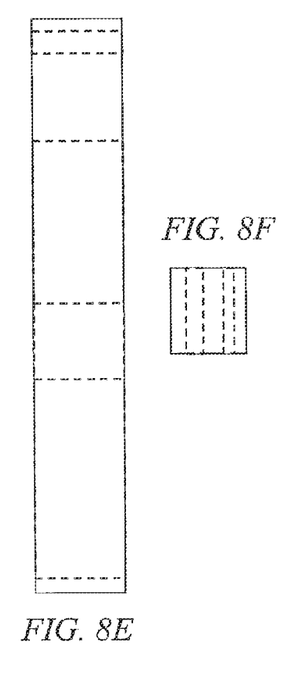
FIG. 8E is a side elevational view of the cutting jig depicted in FIG. 8D.
FIG. 8F is an end view of the cutting jig depicted in FIGS. 8D and 8E.
Figure 8G:
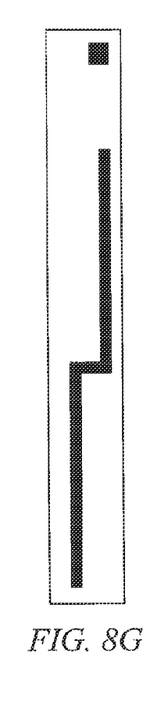
FIG. 8G is a top plan view of a third novel back table allograft cutting jig.
Figure 8H:
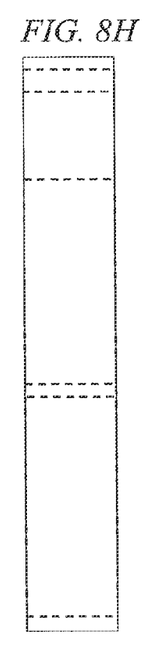
FIG. 8H is a side elevational view of the cutting jig depicted in FIG. 8G.
Figure 8I:
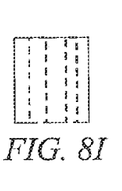
FIG. 8I is an end view of the cutting jig depicted in FIGS. 8G and 8H.

Third pair of stainless steel blocks 56 is slideably mounted in the upper groove as depicted. Blocks 56 hold cutting jigs 57. Multiple cutting jigs are available, depending on whether the surgeon desires a transverse cut (see FIGS. 8A-C), a step cut (FIGS. 8D-F), or a notch cut (FIGS. 8G-I). The cutting jigs are mounted to cylinder 56 which, prior to being locked down by a threaded handle, are rotated to adjust the angle of cut, if desired. A pointer at the base of the cylinder indicates the selected angle. A cutting jig 57 is mounted to each movable stainless steel block 56. A cutting jig for a transverse cut is depicted but multiple cutting jigs are available, depending on whether the surgeon desires a transverse cut, a step cut, or a notch cut, as aforesaid. Arms hold bone clamps 60 for the clamping of the allograft specimen for cutting. The arms have lockable pivots (see transverse lines) that enable adjustments in clamp location. The pointer indicates the position of the cutting jig in reference to the ruler. Wing nuts 11 secure all adjustable components against movement.

Figure 7:
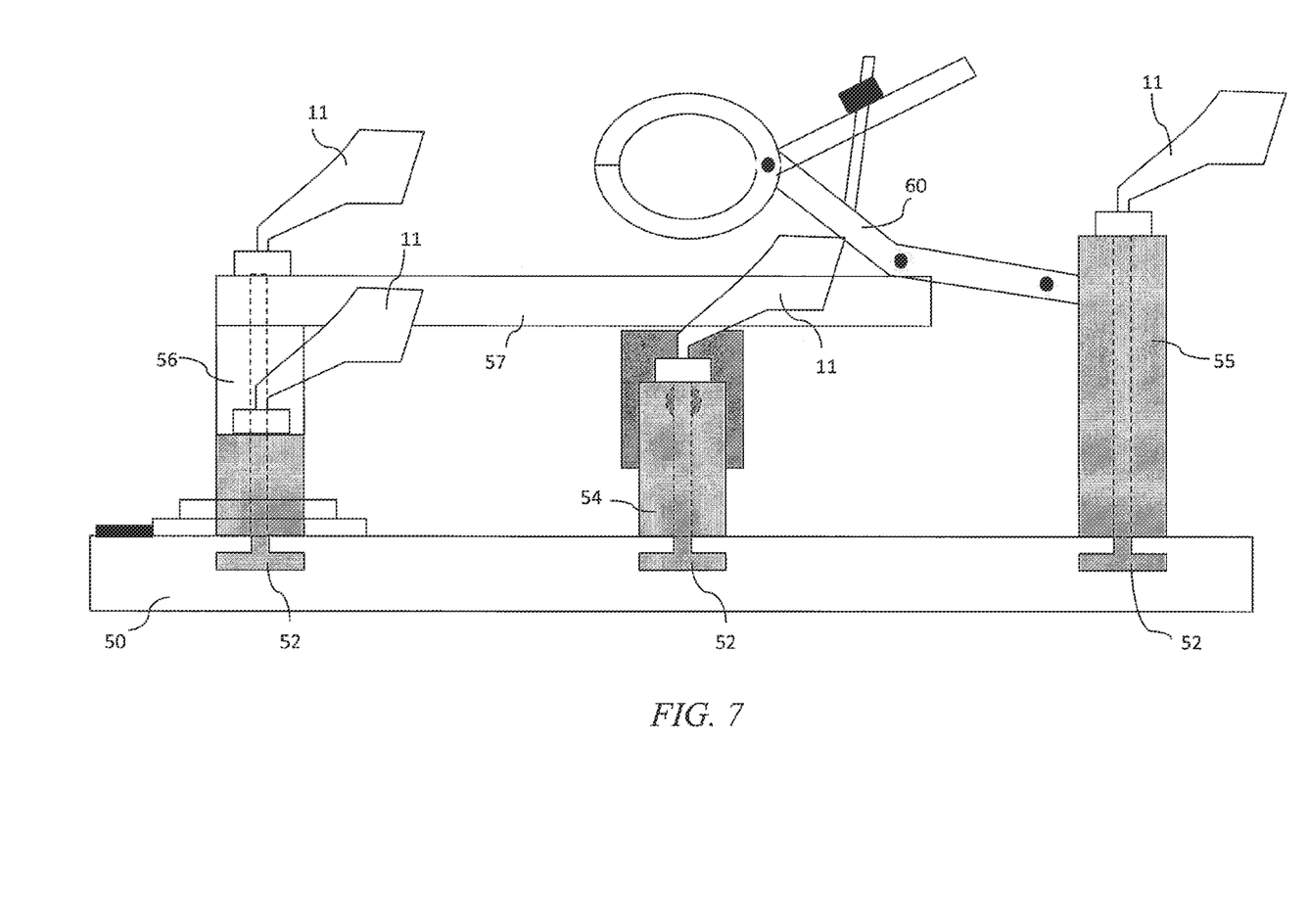
FIG. 7 is an end view of the structure depicted in FIG. 6.

FIG. 7 depicts the allograft cutting device in end view.

FIGS. 8A-I depicts the cutting jigs for the back table graft preparation device. These enable transverse (FIGS. 8A-C), notch (FIGS. 8D-F), and step cuts (FIGS. 8G-I) of the graft ends.

It will thus be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. An apparatus for cutting a graft material and fabricating an allograft therefrom, comprising:
   a surface having a plurality of elongate grooves disposed therein, said plurality of elongate grooves positioned in substantially parallel relation to each other within said surface;
   a first pointed rod secured in and slidably disposed above a first groove of said plurality of grooves in proximity to a first end of said first groove;
   a second pointed rod secured in and slidably disposed above said first groove in proximity to a second end of said first groove, said first and second pointed rods securing said graft material in place by holding said graft material in place in overlying relation to said first groove; and
   a cutting jig secured in and slidably disposed above a second groove of said plurality of grooves, said cutting jig being angled relative to a longitudinal extent of said second groove, such that said graft material can be cut in overlying relation to said first groove.

2. An apparatus as in claim 1, further comprising:
   a second cutting jig secured in and slidably disposed above said second groove, said second cutting jig being angled relative to said longitudinal extent of said second groove, such that said graft material can be cut an additional time in overlying relation to said first groove.

3. An apparatus as in claim 1, further comprising:
   a bone clamp secured in and slidably disposed above a third groove of said plurality of grooves, said bone clamp being angled relative to a longitudinal extent of said third groove, such that said bone clamp can hold said graft material in overlying relation to said first groove.

4. An apparatus as in claim 2, further comprising:
   a first bone clamp secured in and slidably disposed above a third groove of said plurality of grooves, said first bone clamp being angled relative to a longitudinal extent of said third groove, such that said first bone clamp can hold said graft material in overlying relation to said first groove; and
   a second bone clamp secured in and slidably disposed above said third groove, said second bone clamp being angled relative to said longitudinal extent of said third groove, such that said second bone clamp can hold said graft material in overlying relation to said first groove, said first and second bone clamps being positioned to the outside of said cutting jig and said second cutting jig above said first groove.

5. An apparatus as in claim 3, further comprising:
said first groove being positioned between said second and third grooves along said surface.

6. An apparatus as in claim 1, further comprising:
said first and second pointed rods each secured in said first groove via a block with an attachment component positioned within said first groove.

7. An apparatus as in claim 1, further comprising:
said cutting jig secured in said second groove via a block with an attachment component positioned within said second groove.

8. An apparatus as in claim 3, further comprising:
said bone clamp secured in said third groove via a block with an attachment component positioned within said third groove.

9. An apparatus as in claim 1, further comprising:
said first and second grooves each having an upper portion and a lower portion, said lower portion being wider than said upper portion, said upper portion leading to an environment above said first and second grooves, respectively.

10. An apparatus as in claim 9, further comprising:
said upper and lower portions collectively forming an inverted T-shaped groove,
said first and second pointed rods each secured in said first groove via a T-shaped pin that fits within said inverted T-shaped groove of said first groove, and
said cutting jig secured in said second groove via a T-shaped pin that fits within said inverted T-shaped groove of said second groove.

11. An apparatus for cutting a graft material and fabricating an allograft therefrom, comprising:
a surface having a plurality of elongate grooves disposed therein, said plurality of elongate grooves positioned in substantially parallel relation to each other within said surface;
a bone clamp secured in and slidably disposed above a first groove of said plurality of grooves, said bone clamp being angled relative to a longitudinal extent of said first groove, such that said bone clamp can hold said graft material in overlying relation to said surface;
a cutting jig secured in and slidably disposed above a second groove of said plurality of grooves, said cutting jig being angled relative to a longitudinal extent of said second groove, such that said graft material can be cut between said first and second grooves; and
a second bone clamp secured in and slidably disposed above said first groove, said second bone clamp being angled relative to said longitudinal extent of said first groove, such that said second bone clamp can hold said graft material between said first and second grooves.

12. An apparatus as in claim 11, further comprising:
a second cutting jig secured in and slidably disposed above said second groove, said second cutting jig being angled relative to said longitudinal extent of said second groove, such that said graft material can be cut between said first and second grooves.

13. An apparatus as in claim 12, further comprising:
said bone clamp and said second bone clamp both being positioned to the outside of said cutting jig and said second cutting jig between said first and second grooves.

14. An apparatus as in claim 11, further comprising:
a first pointed rod secured in and slidably disposed above a third groove of said plurality of grooves in proximity to a first end of said third groove;
a second pointed rod secured in and slidably disposed above said third groove in proximity to a second end of said third groove, said first and second pointed rods securing said graft material in place by holding said graft material in place in overlying relation to said third groove.

15. An apparatus as in claim 14, further comprising:
said third groove being positioned between said first and second grooves along said surface.

16. An apparatus as in claim 11, further comprising:
said bone clamp secured in said first groove via a block with an attachment component positioned within said first groove.

17. An apparatus as in claim 11, further comprising:
said cutting jig secured in said second groove via a block with an attachment component positioned within said second groove.

18. An apparatus as in claim 14, further comprising:
said first and second pointed rods each secured in said third groove via a block with an attachment component positioned within said first groove.

19. An apparatus as in claim 11, further comprising:
said first and second grooves each having an upper portion and a lower portion, said lower portion being wider than said upper portion, said upper portion leading to an environment above said first and second grooves, respectively.

20. An apparatus as in claim 19, further comprising:
said upper and lower portions collectively forming an inverted T-shaped groove,
said bone clamp secured in said first groove via a T-shaped pin that fits within said inverted T-shaped groove of said first groove, and
said cutting jig secured in said second groove via a T-shaped pin that fits within said inverted T-shaped groove of said second groove.

21. An apparatus for cutting a graft material and fabricating an allograft therefrom, comprising:
a surface having a plurality of elongate grooves disposed therein, said plurality of elongate grooves positioned in substantially parallel relation to each other within said surface;
a first pointed rod secured in and slidably disposed above a first groove of said plurality of grooves in proximity to a first end of said first groove;
a second pointed rod secured in and slidably disposed above said first groove in proximity to a second end of said first groove, said first and second pointed rods securing said graft material in place by holding said graft material in place in overlying relation to said first groove,
said first and second pointed rods each secured in said first groove via a block with an attachment component positioned within said first groove;
a first cutting jig secured in and slidably disposed above a second groove of said plurality of grooves, said first cutting jig being angled relative to a longitudinal extent of said second groove, such that said graft material can be cut a first time in overlying relation to said first groove;
a second cutting jig secured in and slidably disposed above said second groove, said second cutting jig being angled relative to said longitudinal extent of:

said second groove, such that said graft material can be cut an additional time in overlying relation to said first groove, said first and second cutting jigs secured in said second groove via a block with an attachment component positioned within said second groove;

a first bone clamp secured in and slidably disposed above a third groove of said plurality of grooves, said first bone clamp being angled relative to a longitudinal extent of said third groove, such that said first bone clamp can hold said graft material in overlying relation to said first groove; and a second bone clamp secured in and slidably disposed above said third groove, said second bone clamp being angled relative to said longitudinal extent of said third groove, such that said second bone clamp can hold said graft material in overlying relation to said first groove, said first and second bone clamps each secured in said third groove via a block with an attachment component positioned within said third groove, said first and second bone clamps being positioned to the outside of said cutting jig and said second cutting jig above said first groove, said first groove being positioned between said second and third grooves along said surface, said first, second, and third grooves each having an upper portion and a lower portion, said lower portion being wider than said upper portion, said upper portion leading to an environment above said first and second grooves, respectively, said upper and lower portions collectively forming an inverted T-shaped groove, said first and second pointed rods each secured in said first groove via a T-shaped pin that fits within said inverted T-shaped groove of said first groove, and said cutting jig secured in said second groove via a T-shaped pin that fits within said inverted T-shaped groove of said second groove.

\* \* \* \* \*